United States Patent [19]

Mitsuhashi et al.

[11] Patent Number: 4,474,756
[45] Date of Patent: Oct. 2, 1984

[54] PROCESS FOR THE PRODUCTION OF ANTI-HUMAN PROTEIN ANTIBODY

[75] Inventors: Masakazu Mitsuhashi; Shunsaku Koyama, both of Okayama, Japan

[73] Assignee: Kabushiki Kaisha Hayashibara Seibutsu Kagaku Kenkyujo, Okayama, Japan

[21] Appl. No.: 336,942

[22] Filed: Jan. 4, 1982

[30] Foreign Application Priority Data

Feb. 6, 1981 [JP] Japan .................................. 56-15812

[51] Int. Cl.$^3$ ................. A61K 39/395; A61K 39/385; C07G 7/00
[52] U.S. Cl. ................................. 424/85; 260/112 R; 424/88
[58] Field of Search ................... 424/85-92, 424/177, 180, 94; 260/112 R

[56] References Cited

U.S. PATENT DOCUMENTS

| | | | |
|---|---|---|---|
| 3,639,213 | 2/1972 | Ginger et al. | 424/94 |
| 4,041,152 | 8/1977 | Chany et al. | 424/85 |
| 4,172,124 | 10/1979 | Koprowski et al. | 424/85 |
| 4,185,090 | 1/1980 | McIntire | 424/94 |
| 4,196,265 | 4/1980 | Koprowski et al. | 424/85 |
| 4,238,473 | 12/1980 | Lemieux et al. | 424/85 |
| 4,364,935 | 12/1982 | King et al. | 424/85 |

OTHER PUBLICATIONS

Svenson, S., et al., J. Immunological Methods, vol. 25, pp. 323-335, 1979.
Jörbeck, H., et al., J. Immunology, vol. 123, pp. 1376-1381, 1979.
Kohler, G., et al., "Continuous Cultures of Fused Cells Secreting Antibody of Predefined Specificity", Nature, vol. 256, pp. 495-497, (1975).
Davidson, R. L., et al., "Improved Techniques for the Induction of Mammalian Cell Hybridization by Polyethylene Glycon", Somatic Cell Genetics, vol. 2, No. 2, pp. 165-176, (1976).

Primary Examiner—Blondel Hazel
Attorney, Agent, or Firm—Browdy and Neimark

[57] ABSTRACT

The present invention relates to a process for the production of anti-human protein antibody, comprising induction of the antibody production in non-human warm-blooded animal cells capable of producing said antibody by injecting into a non-human warm-blooded animal a human protein-saccharide conjugate, obtained by covalent attachment of a human protein with a saccharide, and harvesting the resulting anti-human protein antibody. The antibody, prepared according to the invention, contains an extremely higher amount of immunoglobulin G than that obtained by conventional method while it contains slight or substantially no immunoglobulin E. Therefore, the antibody can be used advantageously for diagnostic, prophylactic or therapeutic administration in the prevention and treatment of human diseases.

7 Claims, No Drawings

PROCESS FOR THE PRODUCTION OF ANTI-HUMAN PROTEIN ANTIBODY

DETAILED DESCRIPTION OF THE INVENTION

The present invention relates to a process for the production of anti-human protein antibody (referred as "ANTIBODY" hereinafter).

Conventionally, ANTIBODY has been prepared by injecting a human protein into a non-human warm-blooded animal, and harvesting the resulting ANTIBODY from its serum.

However, the conventional processes are disadvantageously difficult to scale-up to a mass production of ANTIBODY in high purity because (1) the process usually require a large amount of human protein, which acts as an antigen in the production of ANTIBODY, (2) the injection of the protein into a non-human warm-blooded animal often causes anaphylactic shock and subsequent death, and because (3) only a small amount of ANTIBODY can be produced thereby, and said ANTIBODY is often contaminated.

The present invention have investigated processes for the production of ANTIBODY wherein the above disadvantages are overcome. These efforts have resulted in the finding that a great amount of ANTIBODY having a high purity and specificity can be obtained easily, with a stronger induction of the ANTIBODY production, in non-human warm-blooded animal cells capable of producing said ANTIBODY, by injecting into a non-human warm-blooded animal a human protein-saccharide conjugate, obtained by covalent attachment of a human protein with a saccharide. The resulting ANTIBODY reacts specifically on the human protein.

Particularly, according to the present invention, ANTIBODY production is extremely enhanced, about 4-100-fold higher than in the case of using an unconjugated human protein, and the enhancement is due to the formation of a great amount of immunoglobulin G while the formation of immunoglobulin E which causes anaphylactic shock is extremely suppressed or substantially dimished therein. Therefore, mass production of ANTIBODY using a non-human warm-blooded animal can be advantageously carried out without fear of anaphylactic shock and/or allergic diseases to the animal.

The term human proten, used in the present specification means a human protein or proteinic substance which is derived from certain human tissue or body fluid, and which acts as an antigen in the production of ANTIBODY in a non-human warm-blooded animal upon its injection. Applicable human proteins are enzymes, hormones, lymphokines, immunoglobulins, serum and components of blood, malignant tumor, urine, sweat, endometrium, placenta and seminal fluid, which are usually purified, prior to the covalent attachment to a saccharide, by one or more procedures selected from the group comprising filtration, washing, centrifugation, salting-out, adsorption and desorption with adsorbent, gel filtration, ion exchange chromatography, affinity chromatography and electrophoresis.

The term saccharide used in the present specification means various polysaccharides such as starch, amylose, dextran, polysucrose or FICOLL (registered trade mark of Pharmacia Fine Chemicals AB, Uppsala, Sweden), pullulan, elsinan, curdlan, gum arabic, tragacanth gum, guar gum, xanthan gum, cellulose, glucomannan, chitosan and partial hydrolysates of any of the above polysaccharides, having an average molecular weight of about 1,000-10,000,000, preferably about 10,000-1,000,000. Especially, the use of non-ionic pullulan, elsinan or their partial hydrolysates, substantially consisting of repeating maltotriose units, after covalent attachment to the human protein advantageously results in an extreme enhancement of the immunoglobulin G formation which specifically reacts with the human protein, and either in a remarkable reduction of the anaphylactic shock-causing immunoglobulin E.

As to the methods for covalent attachment employable in the present invention, any method can be employed as long as it forms covalent linkage(s) between the human protein and the saccharide. Preferable methods are diazo, peptide, alkylation, cross-linking and disulfide methods.

The functional groups usable in the diazo method are p-aminobenzyl, p-aminobenzoyl, m-aminobenzyl, m-aminobenzoyl, m-aminoanisoyl, m-aminobenzyl oxymethyl, 3-(p-aminophenoxy)-2-hydroxy propyonyl, 3-(p-amino-m-methyl anilino)-5-chloro triazinyl and other aromatic amino groups. The saccharide derivatives into which such groups have been introduced according to conventional methods readily effect a coupling reaction with human proteins to form a human protein-saccharide conjugate.

The saccharides usable in the peptide method are carbonate derivatives, such as acid azide, acid chloride, carbodiimide, isocyanate and imido ester including BrCN-activated saccharides such saccharides act as an activated-saccharide in the conjugation reaction with a human protein.

The saccharides usable in the alkylation method are alkyl halide derivatives, such as chloroacetyl, bromoacetyl, iodoacetyl and triazinyl halide derivatives such saccharides preferably effect alkylation reaction with a human protein.

The cross-linking methods employable in the present invention include the cross linkage formation between a human protein and a saccharide in the presence of cross-linking agent, such as glutaraldehyde, glyoxal, succindialdehyde, hexamethylene diisocyanate, toluene 2,4-diisocyanate, bis-azobenzidine or N,N'-ethylene-bis-maleimide.

The preferable weight ratio of the human protein to the saccharide falls in the range from 1:1,000 to 1,000:1 preferably 1:100 to 100:1.

The reaction conditions at which the covalent attachment is effected are about 0°-100° C. for reaction temperature, about 3-12 for reaction pH, and about 0.1-50 hours for reaction time.

The human protein-saccharide conjugate thus obtained can be used intact in the subsequent steps, or purified partially, if necessary, by fractionation by molecular weight, such as gel filtration, prior to the induction of ANTIBODY production.

As to the methods for induction of ANTIBODY production in the non-human warm-blooded animal, any method can be employed as long as the induction takes place thereby. For example, an aqueous solution, emulsion or suspension of the human protein-saccharide conjugate may be injected intravenously, intraperitoneally or subcutaneously into a non-human warm-blooded animal, such as a chicken, pigeon, dog, cat, monkey, goat, pig, cow, horse, rabbit, guinea pig, rat, nude rat, hamster, mouse or nude mouse. The animal is then fed for 3 or more days to effect therein the induction of ANTIBODY production. The injection may be repeated, if necessary, at intervals of about three to thirty days to further enhance the induction.

After the strong induction of ANTIBODY production according to the present invention, the ANTIBODY released in the serum of the animal is harvested, and purified according to conventional methods.

An ANTIBODY preparation having a higher specificity can be obtained by in vitro or in vivo cultivation of certain hybridoma cells obtained by a cell fusion method, for example, that reported in Kohler et al., Nature, Vol. 256, pp. 495–497 (1975) and Eur. J. Immunol., Vol. 6, pp. 511–519 (1976). Spleen cells from the animal which has been subjected to the induction of ANTIBODY production are fused to myeloma cells of the same or different species, and the resulting hybridoma cell line capable of producing said ANTIBODY is cloned and ANTIBODY from the culture product is harvested. The in vivo method to be described below, is preferred as it requires no or much less nutrient medium containing serum for the cell multiplication, and realizes a higher cell multiplication efficiency of the hybridoma cells, and higher ANTIBODY production thereby than in the case of in vitro method.

In the case of the in vivo method, the hybridoma cells are multiplied by implanting them in a non-human warm-blooded animal of the same species as the one used in the induction of ANTIBODY production, or, alternatively, the cells are allowed to multiply in a diffusion chamber through which the nutrient body fluid, such as ascite and/or blood, is supplied to the cells, and the resulting ANTIBODY is collected from said body fluid. Alternatively, hybridoma cells which have been multiplied in vivo may then be subjected to a short-term in vitro cultivation in a serum-free medium for one to five days followed by harvest of the resulting ANTIBODY from the culture medium.

The ANTIBODY thus obtained can be collected easily by conventional purification and separation procedures such as salting-out, dialysis, filtration, centrifugation, concentration and/or lyophilization. If a further purified ANTIBODY preparation is desirable, a preparation of the highest purify can be obtained by the above mentioned procedure(s) in combination with other conventional procedure(s) such as adsorption and desorption with ion exchange, gel filtration, affinity chromatography and/or electrophoresis.

The ANTIBODY preparation, obtained according to the present invention, can be used advantageously for diagnostic, prophylactic or therapeutic administration in the prevention and treatment of human diseases as well as in affinity chromatography using an immobilized ANTIBODY as a ligand.

Throughout the present invention, the ANTIBODIES which specifically react with the human protein were determined by the methods as described previously: immunoglobulin G was assayed by the Passive Haemagglutination (PHA) reaction as described in Japan J. Med. Sci. Biol., Vol. 28, page 127 (1975); and immunoglobulin E, by the Passive Cutaneous Anaphylaxis (PCA) reaction as described in Life Schience, Vol. 8, page 813 (1969).

Several embodiments of the invention are disclosed hereinafter.

EXAMPLE 1

Anti-human interferon antibody

1—(1). Preparation of a human interferon.

The human interferon used in this example was obtained according to the method as disclosed in U.S. Pat. No. 4,276,282.

After preinjection of antiserum, prepared from rabbit according to conventional methods, into newborn hamsters to reduce their possible immunoreactions, were a human leukemic lymphoblastoid line BALL-1 was implanted subcutaneously into the animals, and they were fed in the usual way for three weeks. The resulting massive tumors, formed subcutaneously and about 30 g each, were extracted, and disaggregated by mincing and suspending in a physiological saline solution containing trypsin.

After suspending the trypsinized cells in RPMI medium, supplemented with 10 v/v % foetal calf serum, to give a cell concentration of about $10^7$ cells per ml, the cell suspension was primed with a human lymphoblastoid interferon, 100 IU per ml medium, and then Sendai virus was added, 500 haemagglutination titers per ml medium, followed by 20 hour incubation of the suspension at 37° C. to produce human interferon. Thereafter, the cells were centrifuged, and the supernatant was collected.

After inactivation of the residual Sendai virus in the supernatant by standing at pH 2.0, the resultant was adsorbed at pH 4.0 on SP-Sephadex C-25, registered trade mark of Pharmacia Fine Chemicals AB, Uppsala, Sweden, and then eluted at pH 8.0. The eluate was subjected to gel filtration with Sephadex G-100, also registered trade mark of Pharmacia Fine Chemicals AB, to obtain a fraction containing human interferon. The fraction was lyophilized, and the resultant was dissolved and applied on SP-Sephadex C-25. The resulting eluate containing human interferon was finally dialyzed and lyophilized to obtain an interferon preparation having a specific activity of about $5 \times 10^7$ IU per mg protein.

The interferon yield was about 0.8 mg per animal.

1—(2). Preparation of a human interferon-pullulan conjugate.

An aqueous solution, prepared by dissolving 5 g pullulan, average molecular weight, about 140,000, into 400 ml water, was adjusted to pH 10.7 with 1 N sodium hydroxide, and then 3 g BrCN was added gradually while keeping this pH level, followed by one hour standing under the conditions to effect BrCN-activation reaction. Thereafter, the solution was adjusted to pH 5.0 with 1 N hydrochloric acid, and dialyzed against cold water at this pH level to obtain a BrCN-activated pullulan solution.

To the solution was added 50 mg of the human interferon in 50 ml water, and the resulting mixture was subjected to conjugation reaction under ambient conditions for 24 hours. The resultant was precipitated with three volumes of actone, and the precipitate was collected and dissolved in 0.01 M phosphate buffer (pH 7.0), followed by centrifugation of the resultant to remove insoluble substances. The supernatant was subjected to gel filtration, careful filtration with a membrane filter, and concentration in the given order to obtain a human interferon-pullulan conjugate.

The yield was about 70% against the human interferon used.

1—(3). Preparation of an anti-human interferon antibody.

After preparing with saline an isotonic interferon-pullulan conjugate solution, 0.2 ml aliquots of the solution, protein content about 30 μg, were injected intravenously into hamsters which were then reinjected with the solution seven days after the first injection, and fed for an additional ten days, followed by bleeding of the animals. The blood was pooled and centrifuged to obtain serum which was then precipitated with ammonium sulfate. The fraction obtained at 30–50% saturation was collected and dialyzed. The resultant was purified by affinity chromatography using immobilized human interferon, prepared by coupling reaction of the human interferon with BrCN-activated Sepharose gel at room temperature, to obtain a fraction containing the anti-human interferon antibody. The fraction was dialyzed, and lyophilized to obtain the objective anti-human interferon antibody.

Control ANTIBODY was obtained similarly as above except that the conjugate was replaced with the intact human interferon.

The ANTIBODY preparation, obtained in this example contained more immunoglobulin G, about 30-fold higher per animal, than the control ANTIBODY, and slight immunoglobulin E was found therein. On the other hand, a large amount of immunoglobulin E was found in the control ANTIBODY along with the presence of immunoglobulin G.

The ANTIBODY can be advantageously used for affinity chromatographic purification in the mass production of a highly purified human interferon when immobilized onto a carrier.

EXAMPLE 2

Anti-human urokinase antibody

2—(1). Preparation of a human urokinase.

A human urine urokinase, purchased from Sigma Chemical Company, St. Louis, Mo., USA, was purified similarly as in EXAMPLE 1—(1) by adsorption and desorption with SP-Sephadex C-25, and gel filtration using Sephadex G-100. Thereafter, the fraction containing human urokinase was lyophilized to obtain a human urokinase preparation having a specific activity of about four units per mg protein.

2—(2). Preparation of a human urokinase-elsinan conjugate.

An aqueous elsinan solution was prepared by dissolving 8 g elsinan, average molecular weight, about 800,000, into 200ml hot water, and cooling to room temperature 10 w/v % cyanuryl chloride in 40 ml dimethyl formamide was added to the elsina solution. The mixture was then subjected to activation reaction at room temperature for two hours while keeping the pH level at 7.0 with 1 N sodium carbonate, and the resultant was dialyzed at this pH and 4° C. against water overnight to obtain an activated elsinan solution.

30 mg of the human urokinase in 40 ml water was added to the solution, and the resulting mixture was stirred therein at pH 9.0 for two hours to effect conjugation reaction. The resultant was purified and concentrated similarly as in EXAMPLE 1—(2) to obtain an urokinase-elsinan conjugate.

The yield was about 60% against the human urokinase used.

2—(3). Preparation of an anti-human urokinase antibody.

Rats were injected subcutaneously with 0.3 ml aliquots of complete Freund's adjuvant of the human urokinase-elsinan conjugate, protein content about 20 μg, and then treated similarly as in EXAMPLE 1—(3) to obtain their sera. The sera were pooled, and subjected to salting-out, dialysis, affinity chromatographic purification, dialysis and lyophilization in this order to obtain the objective anti-human urokinase antibody.

Control ANTIBODY was obtained similarly as above except that the conjugate was replaced with the intact human urokinase preparation.

The ANTIBODY preparation, obtained in this example, contained more immunoglobulin G, about 16-fold higher per animal, than the control ANTIBODY, and slight immunoglobulin E was found therein. On the other hand, a large amount of immunoglobulin E was found in the control ANTIBODY along with the presence of immunoglobulin G.

The ANTIBODY cna be advantageously used for affinity chromatographic purification as a ligand in the mass production of a highly-purified human urokinase preparation when immobilized onto a carrier.

EXAMPLE 3

Anti-human lymphocyte antibody

3—(1). Preparation of a human lymphoblastoid protein

A human leukemic lymphoblastoid line BALL-1 was multiplied in Eagle's medium, supplemented with 5 v/v % human serum, and the multiplied human cells were harvested by centrifugation. The cells were then ultrasonicated, 20 KHz, for ten minutes, and centrifuged at 5,000 ×g for 20 minutes. Thereafter, the resulting supernatant was precipitated with ammonium sulfate, and the fraction obtained at 25–80 % saturation, was collected, dialyzed, concentrated and lyophilized to obtain a human lymphoblastoid protein.

3—(2). Preparation of a human lymphoblastoid protein-partial pullulan hydrolysate conjugate.

A pullulan solution was prepared by dissolving 5.2 g partial pullulan hydrolysate, average molecular weight about 10,000, in 110 ml dimethyl formamide while heating, and cooling to room temperature. 10 ml pyridine was added to the pullulan solution. 1.0 g p-nitrobenzoyl chloride was further added to the pullulan solution under stirring conditions, and solution allowed to stand therein at room temperature for 17 hours. Thereafter, two volumes of n-propyl alcohol were added to the reaction mixture, and the resulting precipitate was collected and dissolved in dimethyl formamide. The above precipitation and dissolution operations were repeated three times. The finaly obtained precipitate was dissolved in 100 ml aqueous sodium dithionite solution, and incubated therein at 80° C. for 30 minutes. The resultant was decolorized with activated carbon, and then precipitated with two volumes of n-propyl alcohol. The obtained precipitate was dialyzed against water overnight.

The aqueous solution of the precipitate was cooled to below 2° C., hydrochloric acid was added to give a concentration of about 0.1 N, followed by gradual addition of 0.1 g sodium nitrite. The mixture was then subjected to diazotization reaction for thirty minutes. The resulting diazonium salt was dialyzed against distilled water at below 2° C. for two hours to obtain a diazonium derivative of the partial pullulan hydrolysate.

To the solution was added 2 g of the human lymphoblastoid protein in 70 ml water, and the resulting mixture was adjusted to ph 8.5 by the addition of sodium carbonate solution, followed by two hours standing at this pH level and 4° C. under stirring conditions to effect the coupling reaction. The resultant was purified and concentrated similarly as in Example 1—(2) to obtain a human lymphoblastoid protein-partial pullulan hydro-lysate conjugate.

The yield was about 40% against the human lymphoblastoid protein used.

3—(3). Preparation of an anti-human lymphocyte antibody.

Mice were injected subcutaneously with 0.2 ml aliquots of complete Freund's adjuvant of the human lymphoblastoid protein-partial pullulan hydrolysate conjugate, protein content, about 20 μg, and then treated similarly as in Example 1—(3) to obtain their sera. The sera were pooled, and subjected to salting-out, dialysis, affinity chromatographic purification, dialysis and lyophilization in the given order to obtain the objective anti-human lymphocyte antibody.

Control ANTIBODY was obtained similarly as above except that the conjugate was replaced with the intact human lymphoblastoid protein preparation.

The ANTIBODY obtained in this example contained more immunoglobulin G, about 24-fold higher per animal, than the control ANTIBODY, and slight immunoglobulin E was found therein. On the other hand, a large amount of immunoglobulin E was found in the control ANTIBODY along with the presence of immunoglobulin G.

Since the ANTIBODY exhibits a comparable immunoreaction with human lymphocyte from peripheral blood as with the human lymphoblastoid protein, it can be advantageously used as an immunosuppressant upon transplantation of human organs or skins.

EXAMPLE 4

Anti-human chorionic gonadotropin antibody

4—(1). Preparation of a human chorionic gonadotropin (HCG).

The hCG used in this example was purchased from Calbiochem Co. Ltd., San Diego, Ca., USA, and its specific activity was about 11,500 IU per mg protein.

4—(2) . Preparation of an hCG-elsinan conjugate.

An aqueous elsinan solution was prepared by dissolving 10 g elsinan, average molecular weight about 200,000, in 200 ml distilled water while heating, and cooling to room temperature. 5g hexamethylene diamine was added to the elsinan solution, followed by pH-adjustment to 11.0 with 1 N sodium hydroxide. 5 g BrCN was added to the mixture and the activation reaction was allowed to proceed for 30 minutes while keeping the pH levels and at a temperature of below 20° C. with the use of an ice-water bath. The reaction mixture was dialyzed against distilled water at 4° C. for one hour to obtain an activated elsinan solution.

2ml of 25w/v % aqueous glutaraldehyde solution and 10 mg of the hCG was added to the activated elsinan solution to give a total volume of about 20 ml, and then 10 ml of 1 M acetate buffer (pH 5.0) was added. The mixture was subjected to conjugation reaction at 4° C. for 24 hours under stirring conditions, and the reaction was suspended by the addition of glycine to give a final concentration of about 1 M and the subsequent 24 hour standing under ambient conditions. The resultant was centrifuged, and the supernatant was purified and concentrated similarly as in example 1—(2) to obtain an hCG -elsinan conjugate.

The yield was about 60% against the hCG used.

4—(3). Preparation of an anti-hCG antibody.

Mice were injected intravenously with 0.2 ml aliquots of the isotonic hCG-elsinan conjugate solution in saline, protein content about 20μg, and then treated similarly as in example 1—(3) to obtain their sera. Thereafter, the sera were pooled, and subjected to salting-out, dialysis, affinity chromatographic purification, dialysis and lyophilization in the given order to obtain the objective anti-hCG antibody.

Control ANTIBODY was obtained similarly as above except that the conjugate was replaced with the intact hCG preparation.

The ANTIBODY preparation, obtained in this example, contained more immunoglobulin G, about 20-fold higher per animal, then the control ANTIBODY, and slight immunoglobulin E was found therein. On the other hand, a large amount of immunoglobulin E was found in the control ANTIBODY along with the presence of immunoglobulin G .

The ANTIBODY van be advantageously used for clinical assay of human urine chorionic gonadotropin.

EXAMPLE 5

Anti-human interferon antibody

5—(1). Preparation of a human interferon.

The human interferon used in this example was obtained by the method as described in example 1—(1).

5—(2). Preparation of a human interferon-dextran conjugate.

A human interferon-dextran conjugate was prepared similarly as in example 1—(2) except that the pullulan was replaced with dextran having an average molecular weight of about 70,000 .

The yield was about 40% against the human interferon used.

5—(3). Preparation of an anti-human interferon antibody.

Mice were injected with an isotonic human interferon-dextran conjugate solution in saline, and their sera were treated to obtain the objective anti-human interferon antibody, similarly as in example 1—(3).

Control ANTIBODY was obtained similarly as above except that the conjugate was replaced with the intact human interferon preparation.

The ANTIBODY, obtained in this example, contained more immunoglobulin G, about 12-fold higher per animal, than the control ANTIBODY, and slight immunoglobulin E was found therein. On the other hand, a large amount of immunoglopbulin E was found in the control ANTIBODY along with the presence of immunoglobulin G.

The ANTIBODY can be advantageously used for affinity chromatographic purification as a ligand.

EXAMPLE 6

Anti-human lymphocyte antibody

After strongly inducing, similarly as in example 3, the production of an anti-human lymphocyte anitbody in mouse cells capable of producing said ANTIBODY by the injection of a human lymphoblastoid protein-partial pullulan hydrolysate conjugate, the spleens of the animals were extracted, minced and disaggregated. The spleen cells and a mouse myeloma line MPC-11, ATCC CCL-167, were suspended together in a vessel with a salt solution, containing 140 mM NaCl, 54 mM KCl, 1 mM $NaH_2PO_4$ and 2 mM $CaCl_2$, to give a respective cell concentration of about $10^4$ cells per ml. Thereafter, the cells were mixed under ice-chilling conditions with a fresh preparation of the same salt solution containing UV-irradiation preinactivated Sendai virus, transferred into a 37° C. incubator about five minutes after the mixing, and stirred therein gently for thirty minutes to effect cell fusion.

Mice were injected intraperitoneally with the resulting hybridoma cells in an amount of about $10^6$ cells per animal, and fed for two weeks. Thereafter, the animals were sacrificed, and their body fluid including ascite and blood was collected. The obtained body fluid was purified and lyophilized similarly as in example 3—(3) to obtain the objective anti-human lymphocyte antibody.

Control ANTIBODY was obtained similarly as above except that the mice from which the spleens were extracted had not been injected with the conjugate but with the intact human lymphoblastoid protein preparation.

The ANTIBODY, obtained in this example, contained more immunoglobulin G, up to about 570-fold higher per animal, than the control ANTIBODY, and no immunoglobulin E formation was found therein. On the other hand, a large amount of immunoglobulin E was found in the control ANTIBODY along with the presence of immunoglobulin G.

EXAMPLE 7

Anti-hCG antibody

After strongly inducing, similarly as in example 4, the production of an anti-hCG antibody in mouse cells capable of producing said ANTIBODY by the injection of an hCG-elsinan conjugate, the spleens of the animals were extracted, minced and disaggregated. The spleen cells were fused with a hybrid mouse myeloma line $P_3$-X63-Ag8, purchased from Flow Laboratories Inc., Maryland, USA, by suspending the cells at 4° C. in a vessel with serum-free Eagle's minimal essential medium (pH 7.2), containing 50 w/v % polyethylene glycol 1000, to give a respective cell concentration of about $10^4$ cells per ml, keeping the medium under these conditions for five minutes, and diluting the medium 20-times with a fresh preparation of the same medium.

The hybridoma cells which grew in a culture medium containing hypoxanthine, aminopterin and thymidine were cloned from the medium according to the method as described in Davison et al., Somatic Cell Genetics, Vol. 2, pp. 175-176 (1976).

The cloned hybridoma cells were then implanted subcutaneously in mice which were then fed similarly as in example 6, and sacrificed to obtain their body fluids. Thereafter, the body fluids were purified and lyophilized similarly as in example 4—(3) to obtain the objective anti-hCG antibody.

Control ANTIBODY was obtained similarly as above except that the mice from which the spleens were extracted had not been injected with the conjugate but with the intact hCG preparation.

The ANTIBODY obtained in this example, contained more immunoglobulin G, up to about 440-fold higher per animal, than the control ANTIBODY, and no immunoglobulin E formation was found therein. On the other hand, a large amount of immunoglobulin E was found in the control ANTIBODY along with the presence of immunoglobulin G.

EXAMPLE 8

Anti-human interferon antibody

After strongly inducing, similarly as in example 5, the production of an anti-human interferon antibody in mouse cells capable of producing said ANTIBODY by the injection of an interferon-dextran conjugate, the spleens of the animals were extracted, minced and disaggregated. Then, the spleen cells were fused similarly as in example 7 with a mouse plasmacytoma line MOPC-31-C, ATCC CCL-130.

The resulting hybridoma cells were then implanted intraperitoneally in mice in an amount of about $5 \times 10^5$ cells per animal, and the animals were fed for two weeks. At the end of the feeding, the multiplied hybridoma cells were harvested from their ascites, and the cells were suspended in Eagle's minimal essential medium (pH 7.2), prewarmed at 37° C., to give a cell concentration of about $5 \times 10^6$ cells per ml. The resulting cell suspension was then placed in a $CO_2$ incubator, containing 5 v/v % $CO_2$, and cultivated therein for two days. Thereafter, the culture product was centrifuged, and the obtained supernatant was precipitated with ammonium sulfate. The fraction obtained at 30-50% saturation was collected, dialyzed and carefully filtered with a membrane filter, followed by lyophilization of the resulting filtrate to obtain the objective anti-human interferon antibody.

Control ANTIBODY was obtained similarly as above except that the mice from which the spleens were extracted had not been injected with the conjugate but with the intact human interferon preparation.

The ANTIBODY obtained in this example contained more immunoglobulin G, up to about 160-fold higher per animal, than the control ANTIBODY, and no immunoglobulin E formation was found therein. On the other hand, a large amount of immunoglobulin was found in the control ANTIBODY along with the presence of immunoglobulin G.

What is claimed is:

1. In a process for producing anti-human protein antibody, which comprises administering a human protein to a non-human warm-blooded animal as an antigen, feeding the animal for a period sufficient to accumulate a substantial amount of anti-human protein antibody in the serum, and harvesting the resultant anti-human protein antibody from the serum, the improvement, whereby the production of immunoglobulin G antibody is extremely enhanced, and whereby the formation of undesirable immunoglobulin E antibody is completely suppressed or diminished, wherein said human protein which is administered to the non-human warm-blooded animal is a human protein-saccharaide conjugate comprising an antigenic human protein covalently attached to a member selected from the group consisting of pullulan, elsinan, their partial hydrolysates and mixtures thereof, having an average molecular weight in the range from 1,000 to 10,000,000.

2. A process as set forth in claim 1, wherein said human protein is a member selected from the group consisting of human interferon, human urokinase, human lymphoblastoid protein and human chorionic gonadotropin.

3. A process as set forth in claim 1, wherein said covalent attachment is effected by a method which is diazo, peptide, alkylation, cross-linking or disulfide method.

4. A human protein-saccharide conjugate consisting of an antigenic human protein covalently attached to a member selected from the group consisting of pullulan, elsinan, their partial hydrolysates and mixtures thereof, having an average molecular weight in the range from 1,000 to 10,000,000.

5. A human protein-saccharide conjugate in accordance with claim 4, wherein said human protein is a member selected from the group consisting of human interferon, human urokinase, human lymphoblastoid protein and human chorionic gonadotropin.

6. A human protein-saccharide conjugate in accordance with claim 4, wherein said covalent attachment is effected by a method which is diazo, peptide, alkylation, cross-linking or disulfide method.

7. An anti-human protein antibody preparation high in immunoglobulin G component and low in immunoglobulin E component produced by the process of claim 1.

* * * * *